United States Patent
Albrecht et al.

(10) Patent No.: US 10,350,099 B2
(45) Date of Patent: Jul. 16, 2019

(54) DEVICES AND METHODS FOR ANCHORING AN ENDOLUMINAL SLEEVE IN THE GI TRACT

(71) Applicant: Ethicon Endo-Surgery, Inc., Cincinnati, OH (US)

(72) Inventors: Thomas E. Albrecht, Campbell, CA (US); Mark S. Zeiner, Mason, OH (US); Jason L Harris, Mason, OH (US); Michael J. Stokes, Cincinnati, OH (US); Mark S. Ortiz, Milford, OH (US); Kevin D. Felder, Cincinnati, OH (US); Michele D'Arcangelo, Rome (IT); James W. Voegele, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1129 days.

(21) Appl. No.: 13/644,175

(22) Filed: Oct. 3, 2012

(65) Prior Publication Data

US 2013/0030350 A1    Jan. 31, 2013

Related U.S. Application Data

(63) Continuation-in-part of application No. 11/469,564, filed on Sep. 1, 2006, now abandoned.

(51) Int. Cl.
*A61F 5/00* (2006.01)
*A61F 2/04* (2013.01)

(52) U.S. Cl.
CPC ...... *A61F 5/0036* (2013.01); *A61F 2002/045* (2013.01)

(58) Field of Classification Search
CPC .................. A61F 5/0036; A61F 5/0076; A61F 2002/0045
See application file for complete search history.

(56) References Cited

U.S. PATENT DOCUMENTS

| 3,583,391 A | 6/1971 | Cox et al. |
| 4,134,405 A | 1/1979 | Smit |

(Continued)

FOREIGN PATENT DOCUMENTS

| DE | 112011102287 T5 | 5/2013 |
| EP | 1708641 | 7/2005 |

(Continued)

OTHER PUBLICATIONS

European Search Report dated Aug. 19, 2009; Application No. 09250720.1.

(Continued)

*Primary Examiner* — Katrina M Stransky
*Assistant Examiner* — Lindsey Bachman (57) ABSTRACT

An endoluminal sleeve device for internally lining a section of the GI tract, comprises a sleeve configured for deployment inside a duodenum, the sleeve having walls of a flexible material defining a sleeve lumen, a proximal end defining a proximal lumen opening, and a distal end defining a distal lumen opening, an anchoring component having a slender transport configuration and a bulky deployed configuration, wherein the anchoring component is locatable at a distance from the proximal sleeve end and connected thereto by an elongated tether.

14 Claims, 9 Drawing Sheets

(56) References Cited

U.S. PATENT DOCUMENTS

| | | | |
|---|---|---|---|
| 4,315,509 A * | 2/1982 | Smit | A61F 5/0076 |
| | | | 417/474 |
| 4,416,267 A | 11/1983 | Garren et al. | |
| 4,479,497 A | 10/1984 | Fogarty et al. | |
| 4,519,392 A | 5/1985 | Lingua | |
| 4,607,618 A | 8/1986 | Angelchik | |
| 4,719,916 A | 1/1988 | Ravo | |
| 4,925,446 A | 5/1990 | Garay et al. | |
| 4,946,440 A | 8/1990 | Hall | |
| 5,129,915 A | 7/1992 | Cantenys | |
| 5,382,231 A | 1/1995 | Shlain | |
| 5,389,089 A | 2/1995 | Bauer et al. | |
| 5,558,665 A | 9/1996 | Kieturakis | |
| 5,624,381 A | 4/1997 | Kieturakis | |
| 5,868,141 A | 2/1999 | Ellias | |
| 6,113,611 A | 9/2000 | Allen et al. | |
| 6,302,917 B1 | 10/2001 | Dua et al. | |
| 6,368,340 B2 | 4/2002 | Malecki et al. | |
| 6,558,400 B2 | 5/2003 | Deem et al. | |
| 6,558,429 B2 | 5/2003 | Taylor | |
| 6,656,194 B1 | 12/2003 | Gannoe et al. | |
| 6,705,989 B2 | 3/2004 | Cuschieri et al. | |
| 6,740,121 B2 | 5/2004 | Geltz | |
| 6,746,460 B2 | 6/2004 | Gannoe et al. | |
| 6,773,440 B2 | 8/2004 | Gannoe et al. | |
| 6,981,978 B2 | 1/2006 | Gannoe | |
| 6,994,715 B2 | 2/2006 | Gannoe et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,044,957 B2 | 5/2006 | Foerster et al. | |
| 7,066,945 B2 | 6/2006 | Hashiba et al. | |
| 7,083,629 B2 | 8/2006 | Weller et al. | |
| 7,097,650 B2 | 8/2006 | Weller et al. | |
| 7,112,058 B2 | 9/2006 | Felix | |
| 7,121,283 B2 | 10/2006 | Stack et al. | |
| 7,122,058 B2 | 10/2006 | Levine et al. | |
| 7,175,638 B2 | 2/2007 | Gannoe et al. | |
| 7,211,094 B2 | 5/2007 | Gannoe et al. | |
| 7,211,114 B2 | 5/2007 | Bessler et | |
| 7,214,233 B2 | 5/2007 | Gannoe et al. | |
| 7,220,237 B2 | 5/2007 | Gannoe et al. | |
| 7,229,428 B2 | 6/2007 | Gannoe et al. | |
| 7,267,694 B2 | 9/2007 | Levine et al. | |
| 7,288,064 B2 | 10/2007 | Boustani et al. | |
| 7,288,099 B2 | 10/2007 | Deem et al. | |
| 7,288,101 B2 | 10/2007 | Deem et al. | |
| 7,306,614 B2 | 12/2007 | Weller et al. | |
| 7,329,285 B2 | 2/2008 | Levine et al. | |
| 7,347,875 B2 | 3/2008 | Levine et al. | |
| 7,476,256 B2 | 1/2009 | Meade et al. | |
| 7,503,922 B2 | 3/2009 | Deem et al. | |
| 7,510,559 B2 | 3/2009 | Deem et al. | |
| 7,608,114 B2 * | 10/2009 | Levine et al. | 623/23.7 |
| 7,678,068 B2 | 3/2010 | Levine et al. | |
| 7,682,330 B2 | 3/2010 | Meade et al. | |
| 7,695,446 B2 | 4/2010 | Levine et al. | |
| 7,708,684 B2 | 5/2010 | Demarais et al. | |
| 7,753,870 B2 | 7/2010 | Demarais et al. | |
| 7,753,928 B2 | 7/2010 | de la Torre et al. | |
| 7,757,924 B2 | 7/2010 | Gerbi et al. | |
| 7,758,535 B2 | 7/2010 | Levine et al. | |
| 7,766,861 B2 | 8/2010 | Levine et al. | |
| 7,766,973 B2 | 8/2010 | Levine et al. | |
| 7,771,382 B2 | 8/2010 | Levine et al. | |
| 7,789,848 B2 | 9/2010 | Gannoe et al. | |
| 7,815,589 B2 | 10/2010 | Meade et al. | |
| 7,815,591 B2 | 10/2010 | Levine et al. | |
| 7,819,836 B2 | 10/2010 | Levine et al. | |
| 7,837,643 B2 | 11/2010 | Levine et al. | |
| 7,837,669 B2 | 11/2010 | Dunn et al. | |
| 7,862,574 B2 | 1/2011 | Deem et al. | |
| 7,909,838 B2 | 3/2011 | Deem et al. | |
| 7,931,693 B2 | 4/2011 | Binmoeller et al. | |
| 7,935,073 B2 | 5/2011 | Levine et al. | |
| 7,967,798 B2 | 6/2011 | Reydel et al. | |
| 7,976,488 B2 | 7/2011 | Levine et al. | |
| 7,981,163 B2 | 7/2011 | Meade et al. | |
| 8,057,420 B2 | 11/2011 | Meade et al. | |
| 8,096,966 B2 | 1/2012 | Levine et al. | |
| 8,109,895 B2 | 2/2012 | Williams et al. | |
| 8,137,301 B2 | 3/2012 | Levine et al. | |
| 8,162,871 B2 | 4/2012 | Levine et al. | |
| 8,303,669 B2 | 11/2012 | Meade et al. | |
| 8,403,877 B2 | 3/2013 | Priplata et al. | |
| 8,425,451 B2 | 4/2013 | Levine et al. | |
| 8,475,401 B2 | 7/2013 | Priplata et al. | |
| 8,486,153 B2 | 7/2013 | Levine et al. | |
| 8,491,519 B2 | 7/2013 | Chin | |
| 8,574,184 B2 | 11/2013 | Errico et al. | |
| 8,591,452 B2 | 11/2013 | Priplata et al. | |
| 8,628,583 B2 | 1/2014 | Meade et al. | |
| 9,237,944 B2 | 1/2016 | Meade et al. | |
| 2001/0018593 A1 | 8/2001 | Nguyen et al. | |
| 2001/0044595 A1 | 11/2001 | Reydel et al. | |
| 2002/0111641 A1 | 8/2002 | Peterson et al. | |
| 2002/0188318 A1 | 12/2002 | Carley et al. | |
| 2004/0092892 A1 | 5/2004 | Kagan et al. | |
| 2004/0107004 A1 | 6/2004 | Levine et al. | |
| 2004/0148034 A1 | 7/2004 | Kagan et al. | |
| 2004/0220682 A1 | 11/2004 | Levine et al. | |
| 2005/0075622 A1 | 4/2005 | Levine et al. | |
| 2005/0080395 A1 | 4/2005 | Levine et al. | |
| 2005/0080431 A1 | 4/2005 | Levine et al. | |
| 2005/0080491 A1 | 4/2005 | Levine et al. | |
| 2005/0085923 A1 | 4/2005 | Levine et al. | |
| 2005/0125020 A1 | 6/2005 | Meade et al. | |
| 2005/0125075 A1 | 6/2005 | Meade et al. | |
| 2005/0277975 A1 | 12/2005 | Saadat et al. | |
| 2006/0009858 A1 | 1/2006 | Levine et al. | |
| 2006/0106288 A1 | 5/2006 | Roth et al. | |
| 2006/0155311 A1 | 7/2006 | Hashiba et al. | |
| 2006/0161187 A1 | 7/2006 | Levine et al. | |
| 2006/0217757 A1 | 9/2006 | Horndeski | |
| 2007/0005147 A1 | 1/2007 | Levine et al. | |
| 2007/0185518 A1 | 8/2007 | Hassier, Jr. | |
| 2007/0239284 A1 | 10/2007 | Skerven et al. | |
| 2007/0250020 A1 | 10/2007 | Kim et al. | |
| 2007/0276428 A1 | 11/2007 | Haller et al. | |
| 2008/0058840 A1 | 3/2008 | Albrecht et al. | |
| 2008/0167629 A1 | 7/2008 | Dunn et al. | |
| 2008/0187206 A1 | 8/2008 | Sendal et al. | |
| 2008/0208357 A1 | 8/2008 | Melanson et al. | |
| 2008/0234834 A1 | 9/2008 | Meade et al. | |
| 2008/0255587 A1 | 10/2008 | Cully et al. | |
| 2008/0255678 A1 | 10/2008 | Cully et al. | |
| 2009/0240340 A1 | 9/2009 | Levine et al. | |
| 2009/0248171 A1 | 10/2009 | Levine et al. | |
| 2010/0256776 A1 | 10/2010 | Levine et al. | |
| 2010/0298632 A1 | 11/2010 | Levine et al. | |
| 2010/0305590 A1 | 12/2010 | Holmes et al. | |
| 2010/0331756 A1 | 12/2010 | Meade et al. | |
| 2011/0004146 A1 | 1/2011 | Priplata et al. | |
| 2011/0004234 A1 | 1/2011 | Priplata et al. | |
| 2011/0004236 A1 | 1/2011 | Priplata et al. | |
| 2011/0046537 A1 * | 2/2011 | Errico et al. | 604/8 |
| 2011/0245752 A1 | 10/2011 | Levine et al. | |
| 2011/0257580 A1 | 10/2011 | Meade et al. | |
| 2011/0276091 A1 | 11/2011 | Melanson et al. | |
| 2011/0301523 A1 | 12/2011 | Levine et al. | |
| 2012/0143348 A1 | 6/2012 | Voegele | |
| 2012/0184967 A1 | 7/2012 | Levine et al. | |
| 2012/0215152 A1 | 8/2012 | Levine et al. | |
| 2013/0012862 A1 | 1/2013 | Meade et al. | |
| 2013/0030350 A1 | 1/2013 | Albrecht et al. | |
| 2013/0253410 A1 | 9/2013 | Levine et al. | |
| 2014/0018719 A1 * | 1/2014 | Chamorro et al. | 604/8 |

FOREIGN PATENT DOCUMENTS

| | | |
|---|---|---|
| EP | 1610720 B1 | 2/2009 |
| EP | 2080242 | 7/2009 |
| EP | 1610719 B1 | 1/2010 |

(56) References Cited

FOREIGN PATENT DOCUMENTS

| | | |
|---|---|---|
| EP | 2139438 | 1/2010 |
| EP | 2280669 | 2/2011 |
| EP | 1768618 B1 | 4/2011 |
| EP | 2382948 A1 | 11/2011 |
| EP | 2103286 B1 | 10/2012 |
| EP | 1850812 B1 | 12/2012 |
| EP | 2394612 B1 | 4/2013 |
| JP | 2010-502312 | 1/2010 |
| JP | 2010104853 A | 5/2010 |
| JP | 2010269158 A | 12/2010 |
| JP | 2011251164 A | 12/2011 |
| JP | 2012152576 A | 8/2012 |
| JP | 2013090940 A | 5/2013 |
| WO | WO 01/35832 A2 | 5/2001 |
| WO | WO 2004049982 A2 | 6/2004 |
| WO | WO 2004/060169 A3 | 7/2004 |
| WO | WO 2004087014 A3 | 10/2004 |
| WO | WO 2005060869 A1 | 7/2005 |
| WO | WO 2005060882 A1 | 7/2005 |
| WO | WO 2006016894 A1 | 2/2006 |
| WO | WO 2006034062 A1 | 3/2006 |
| WO | WO 2006078781 A1 | 7/2006 |
| WO | WO 2006078927 A1 | 7/2006 |
| WO | WO 2006102012 A1 | 9/2006 |
| WO | WO 2006133311 A3 | 12/2006 |
| WO | WO 2007/075978 A2 | 7/2007 |
| WO | WO 2008/028108 A2 | 3/2008 |
| WO | WO 2008/039800 | 4/2008 |
| WO | WO 2009085107 A1 | 7/2009 |
| WO | WO 2011031981 A1 | 3/2011 |
| WO | WO 2011/120047 | 9/2011 |
| WO | WO 2012006146 A1 | 1/2012 |
| WO | WO 2012072133 A1 | 6/2012 |
| WO | WO 2012072134 A1 | 6/2012 |
| WO | WO 2012072136 A3 | 6/2012 |
| WO | WO 2012072137 A1 | 6/2012 |
| WO | WO 2012072138 A1 | 6/2012 |
| WO | WO 2012072662 A1 | 6/2012 |
| WO | WO 2012107079 A1 | 8/2012 |
| WO | WO 2012136249 A1 | 10/2012 |
| WO | WO 2013023675 A1 | 2/2013 |
| WO | WO 2013023676 A1 | 2/2013 |
| WO | WO 2013023679 A1 | 2/2013 |
| WO | WO 2013026473 A1 | 2/2013 |
| WO | WO 2013026474 A1 | 2/2013 |
| WO | WO 2013028837 A1 | 2/2013 |
| WO | WO 2013028841 A1 | 2/2013 |
| WO | WO 2013087092 A1 | 6/2013 |
| WO | WO 2013087093 A1 | 6/2013 |
| WO | WO 2013087095 A1 | 6/2013 |
| WO | WO 2013087096 A1 | 6/2013 |
| WO | WO 2013185830 A1 | 12/2013 |
| WO | WO 2014012041 A1 | 1/2014 |

OTHER PUBLICATIONS

European Search Report dated Jan. 27, 2014; Application No. 07814611.5..
International Preliminary Report dated Mar. 3, 2009; International Application No. PCT/US2007/77351.
International Search Report dated Oct. 1, 2008; International Application No. PCT/US2007/77351.
International Preliminary Report dated Jan. 5, 2011; International Application No. PCT/US2009/048609.
International Search Report dated Dec. 30, 2009; International Application No. PCT/US2009/048609.
EPO Search Report dated Oct. 1, 2008 for corresponding patent application , European Patent Application No. PCT/US07/773251.
International Preliminary Report re: PCT/US2014/052085 dated Mar. 1, 2016.
International Search Report and Written Opinion dated Nov. 12, 2014 for Application No. PCT/US2014/052085.
Supplementary Partial European Search Report re: 07814611 dated Jan. 14, 2014.

* cited by examiner

Fig. 33

DEVICES AND METHODS FOR ANCHORING AN ENDOLUMINAL SLEEVE IN THE GI TRACT

RELATED APPLICATIONS

This is a continuation-in-part of application Ser. No. 11/469,564 filed 1 Sep. 2006, now abandoned, and international application PCT/EP2011/063945 filed 12 Aug. 2011, the contents of which are incorporated by reference.

BACKGROUND

The present invention relates generally to medical apparatuses and methods and more particularly to devices and methods for positioning and anchoring a lining to a hollow body organ, such as a stomach, intestine or gastrointestinal tract.

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Although the outcome of these stomach reduction surgeries leads to patient weight loss because patients are physically forced to eat less due to the reduced size of their stomach, several limitations exist due to the invasiveness of the procedures, including time, general anesthesia, healing of the incisions and other complications attendant to major surgery. In addition, these procedures are only available to severely obese patients (morbid obesity, Body Mass Index >=40) due to their complications, including the risk of death, leaving patients who are considered obese or moderately obese with few, if any, interventional options.

In addition to the above described gastrointestinal reduction surgery, endoluminal sleeves are known for partially or totally lining certain portions of the stomach and of the intestine with the aim to separate or bypass at least part of the food flow from the lined portions of the gastrointestinal tract. It has been observed that by creating a physical barrier between the ingested food and certain regions of the gastrointestinal wall by means of endoluminal sleeves, similar benefits for weight loss and improvement or resolution of type 2 diabetes may be achieved as with gastric bypass surgery. Physicians believe that by creating a physical barrier between the ingested food and selected regions of the gastrointestinal wall, it might be possible to purposefully influence the mechanism of hormonal signal activation originating from the intestine. It was observed that endoluminal sleeves in certain regions of the stomach and the duodenum contributed to improve glycemic control and to reduce or eliminate other co-morbidities of obesity. Moreover the lining of parts of the GI-tract by means of endosleeves provide an alternative or an additional therapy to traditional therapies of type II diabetes and obesity. Endosleeves may be placed in a brief and less invasive procedure and address the patient's fear of surgery. Contrary to traditional gastric bypass surgery, the result of endoluminal sleeve surgery is reversible and the sleeve can be removed after achievement of the clinical result, but also in case of the occurrence of undesired side effects or clinical complications.

A typical duodenal sleeve device is described in U.S. Pat. No. 7,267,694 where the proximal end of a flexible, floppy sleeve of impermeable material defining a sleeve lumen is endoscopically deployed and anchored with the help of a barbed stent in the pylorus or in the superior section of the duodenum, the stent also ensuring that the proximal lumen opening of the sleeve remains open. Chyme from the stomach enters the proximal lumen opening of the sleeve and passes through the sleeve lumen to the distal lumen opening. Digestive enzymes secreted in the duodenum pass through the duodenum on the outside of the sleeve. The enzymes and the chyme do not mix until the chyme exits from the distal lumen opening of the liner tube. In such a way, the efficiency of the process of digestion of the chyme is diminished, reducing the ability of the gastrointestinal tract to absorb calories from the food.

G.I. Dynamics, Inc., (Watertown, Mass., USA) produces the Endobarrier(R) device that is substantially a duodenal sleeve device configured so that the proximal end of the device is anchored inside the duodenal bulb with the help of a barbed anchoring stent that also keeps the proximal lumen opening open.

In US 2004/0148034 is taught a duodenal sleeve device attached to a funnel, the funnel configured for anchored to the gastric walls inside the gastric cavity in proximity to the lower esophageal sphincter. Food passing the lower esophageal sphincter is directed by the funnel into the proximal lumen opening of the duodenal sleeve device.

In U.S. Pat. No. 7,121,283 is taught a duodenal sleeve device attached to a large stent-like anchoring device that presses outwardly against the pyloric portion of the stomach, the pyloric sphincter and the duodenal bulb.

BRIEF DESCRIPTION OF THE DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

DETAILED DESCRIPTION

Referring to the drawings where like numerals denote like anatomical structures and components throughout the several views, an endoluminal sleeve device 1 for internally lining a section of the GI tract, particularly a section of duodenum distally from the pylorus, comprises a sleeve 2 configured for deployment inside a duodenum of a human subject, the sleeve 2 having walls of a flexible material defining a sleeve lumen 3, a proximal end 4 defining a proximal lumen opening 5, and a distal end 6 defining a distal lumen opening 7. The device 1 comprises further an anchoring component 8 having a slender transport configuration and a bulky deployed configuration, the anchoring component 8 being locatable at a distance from the proximal sleeve end 4 and connected thereto by an elongated tether 9.

The anchoring component 8 can be endoluminally inserted in and removed from the stomach 10 through the mouth and the esophagus while being in the slender transport configuration and, thanks to the distance between the anchoring component 8 and the proximal sleeve end 4, the anchoring component 8 can be deformed to the bulky deployed configuration without interfering with or influencing the shape of the proximal lumen opening 5 which is crucial for the sealing of the sleeve 2 against the gastrointestinal wall. Moreover, thanks to the distance between the expandable anchoring component 8 and the proximal sleeve end 4, the anchoring component 8 can bear against selected robust structures of the stomach 10, such as for instance the cardiac portion or the antrum, while staying away from more delicate structures, such as the proximal duodenum and the pyloric valve. In this way the risk of obstruction and trauma by the anchoring component 8 is reduced.

In accordance with an embodiment (FIG. 4), the anchoring component 8 comprises a gastric coil 11 which can change shape from an extended free-ended string shape adapted for transoral or transnasal transportation thereof into the stomach, to an arched or annular configuration adapted to shape connect with the stomach 10 such as to provide an anchor for the pull resistant tether 9 which is connected to the proximal sleeve end 4.

Figure 4:
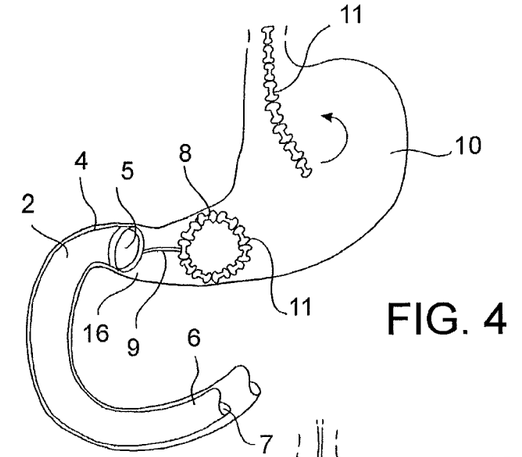
FIG. 4 illustrates a duodenal sleeve device in accordance with a further embodiment and method steps for its endoluminal placement and anchoring in the GI tract.

In accordance with embodiments, the gastric coil 11 can comprise a sequence of rigid segments which are linked to one another by elastic or shape memory or phase changeable material links Additionally or alternatively, the gastric coil 11 can be snap rigidizable in its arched deployed shape, e.g. by means of mutually snap connectable initially free ends, by a pull string activatable rigidizing mechanism.

In case of an open ended arched deployed shape, the free ends are preferably oriented radially inwardly with respect to an outer coil contour in order to not rub and irritate the surrounding tissue.

The free-ended string shape of the gastric coil 11 in the transport configuration provides an extremely slender structure which can be easily and mini-invasively moved through the mouth down the esophagus into the stomach or pushed through an endoluminally or laparoscopically inserted insertion tube.

A proximal tether end of the tether 9 can be connected to a free end of the gastric coil 11 or to an intermediate portion thereof at a distance from both free ends.

In accordance with a further embodiment (FIG. 5), the anchoring component 8 comprises a gastric balloon 12 which can be expanded from a collapsed shape to an expanded shape and which may be dimensioned to occupy a substantial volume of the stomach 10, thereby combining the weight loss effect due to stomach reduction with the function of anchoring the sleeve 2. In the expanded configuration, the gastric balloon 12 may define a through hole 13 that allows the food to flow through the balloon 12 which would otherwise obstruct the stomach 10. In this case a proximal end of tether 9 may be fastened to the gastric balloon 12 near or at a distal aperture 14 of the through hole 13 in order that the distal pulling force due to peristalsis correctly orients the gastric balloon 12 and prevents the through hole opening from being fully covered and obstructed by the gastric wall.

Figure 5:
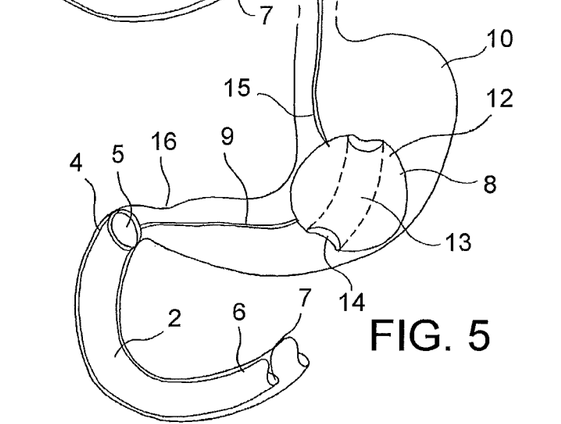
FIG. 5 illustrates a duodenal sleeve device in accordance with a further embodiment anchored within the stomach.

After initial endoscopic inspection of the stomach of a patient, the balloon 12 can be endoscopically passed through the mouth and down the esophagus into the stomach while it is in its smallest, deflated shape. Once the balloon is inside the stomach, it is filled with sterile saline solution through a filling catheter 15 attached to the balloon 12. Once filled, the catheter 15 is removed and the balloon 12, pulled distally by the attached tether 9 engages the stomach wall proximal to the pylorus 16.

The balloon 12 may be grafted of a soft and pliable silicone material similar to known intragastric balloons. Alternatively or additionally, the gastric balloon 12 may have a foldable or stretchable outer wall to which an internal frame (not shown) is attached which is expandable from a collapsed shape to an expanded shape.

In an embodiment, the internal frame can be expanded together with the gastric balloon 12 outer wall by insufflating the balloon e.g. with saline solution. The frame is configured that, after expansion thereof, it preserves the expanded shape of the balloon independently from the insufflating fluid and possible deflation. This will assure a much longer live cycle of the anchoring balloon 12 compared to known gastric balloons.

In a further embodiment, the internal frame may be elastically deformable from a released expanded shape to a compressed collapsed shape and the gastric balloon 12 may be held in the collapsed shape (transport configuration of the anchoring component) by an external retaining device, e.g. a stretch resistant outer sheath, a rigid capsule, a retaining string or retaining band. In this case, expansion of the gastric balloon 12 can be accomplished by removing the retaining device once the gastric balloon is positioned within the stomach. Hence, no insufflations is required.

The gastric balloon 12 can be removed together with the sleeve 2 or independently from the sleeve 2, via the esophagus and mouth. For this purpose, the gastric balloon 12 is deformed, prior to removal, back to its collapsed shape, e.g. by deflation (by means of endoscopic puncturing) and/or external compression. Once the balloon 12 is collapsed it can be endoscopically grasped and removed from the stomach 10 through the esophagus and the mouth.

Figures 1, 2:
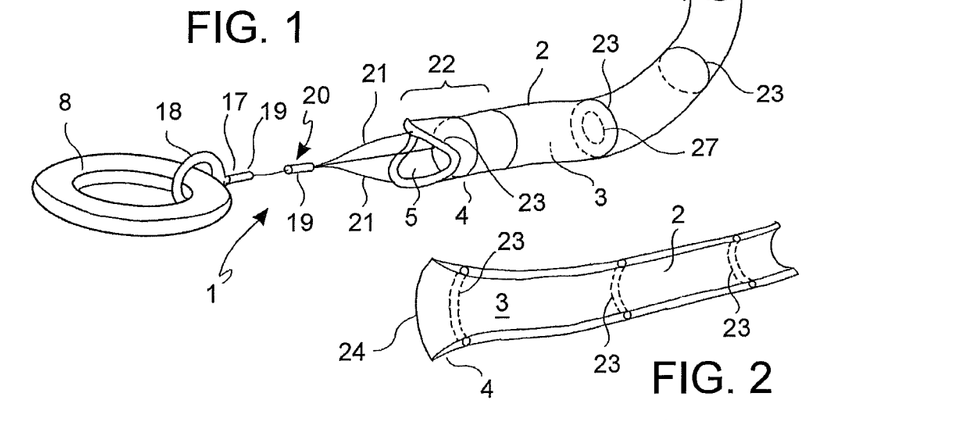
FIG. 1 illustrates a duodenal sleeve device in accordance with an embodiment.
FIG. 2 is a longitudinal cross-section of a sleeve of a duodenal sleeve device in accordance with an embodiment.
Figure 6:
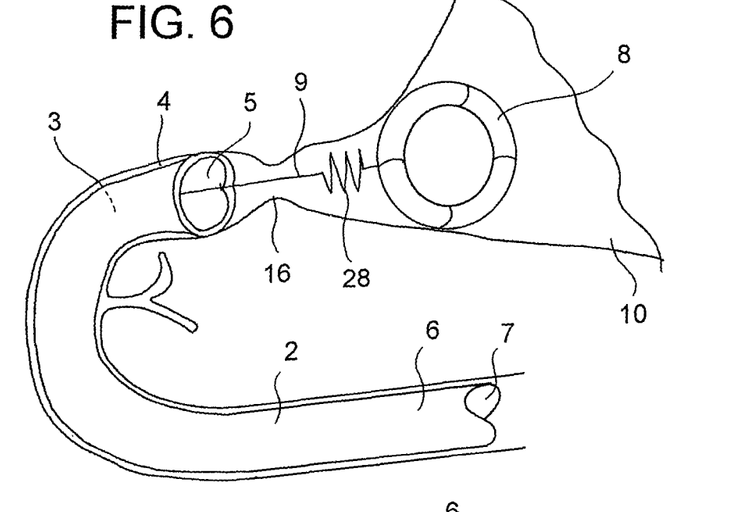
FIG. 6 illustrates a duodenal sleeve device in accordance with a yet further embodiment anchored within the stomach.
Figures 7, 8:
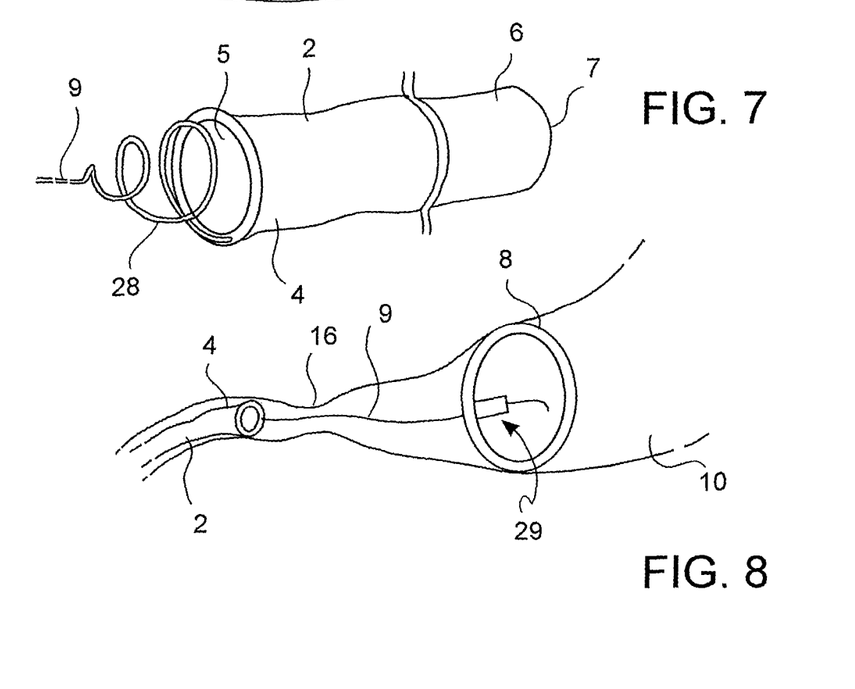
FIG. 7 illustrates a detail of a duodenal sleeve device in accordance with an embodiment.
FIG. 8 illustrates a detail of a duodenal sleeve device in accordance with a further embodiment.
Figure 9:
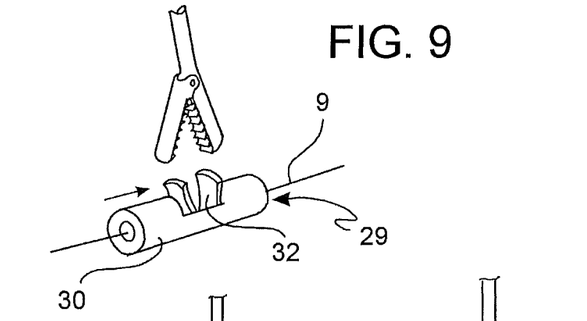
FIGS. 9 through 11 illustrate devices and methods for adjusting the length of a tether of a duodenal sleeve device in accordance with an embodiment.
Figure 10:
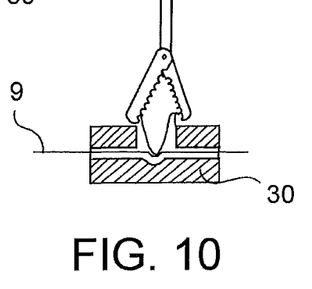
Figure 11:
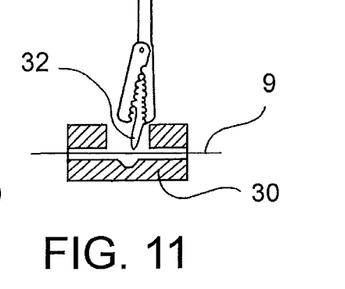

In accordance with a further embodiment, the anchoring component 8 comprises a non deformable monolithic rigid ring or coil which is placed within the stomach through a previously created gastrostomy. The rigid single piece anchoring component reduces the risk of undesired In accordance with a yet further embodiment, the anchoring component 8 comprises a set of individual initially separate segments which are adapted to be individually transportable into the stomach and which can be assembled, e.g. by snap fit and/or additional magnetic attraction to form a rigid body of greater dimensions than the individual segments, particularly a ring or a coil, as illustrated in FIGS. 1, 6, 8.

In accordance with an embodiment (FIG. 1), the anchoring component has an outer wall or external surface layer of non degradable material, such as an austenitic Chromium-Nickel stainless steel with superior corrosion resistance. An example for such a material is SS316L which permits usage in severe corrosive environments and which, for the intended use, may have a nominal composition of Chromium 17.2%, Manganese 1.6%, Nickel 10.9%, Carbon 0.02%, Molybdenum 2.1% +Iron Balance to complete 100%.

The proximal tether end 17 may be connected to the ring or coil shaped anchoring component 8 by a proximal connecting ring 18 which can slide along a section of the anchoring component 8 to assure that the connecting ring 18 can always slide to the most distal located portion of the anchoring component 8. In this way, a rotation of the anchoring component 8 due to movements of the gastric wall or of the pylorus will not substantially change the position of the proximal end 17 of tether 9 and undesired local displacements of the proximal end 4 of the sleeve 2 are significantly reduced.

The connecting ring 18 can be made of the same non degradable material as the anchoring component outer wall, e.g. a welded or braced SS316L wire annulus.

The tether 9 may be a flexible non-stretchable wire or braded cable made from a non-degradable material, such as e.g. the above said SS316L steel alloy or other suitable high corrosion resistant material.

In accordance with an embodiment, an initially free tether end is routed through a crimping tube 19 (which is conveniently of the same material as the tether, i.e. SS316L steel alloy), then around the connecting ring 18 and back through (or into) the crimping tube 19, which is then crimped to lock the tether 9 within the tube and attached to the connecting ring 18. Conveniently, in order to reduce the risk of trauma, the free end of the tether 9 remains encapsulated inside the crimped crimping tube 19.

The described connection solution allows an easy and structurally reliable connection with a possibility to easily adjust the tether length prior to crimping.

The finished assembly can be additionally coated with a silicone coating for protection against the acid environment within the GI tract and for creating a smooth external surface which doesn't irritate the surrounding tissues. The silicone coating may be a combination of a tubing of flexible, inert silicone elastomer, a silicone sealant or adhesive or other protective materials which completely encapsulate the braided cable of the tether 9, the crimping tube 19 and the connecting ring 18.

In the deployed configuration, the tether 9 passes through the pylorus 16 and connects the proximal sleeve end 4 (located within the duodenum) to the anchoring component 8 within the stomach.

A distal tether portion may form junction point 20 from which a plurality of e.g. two to five, preferably 3 or 4, distal split tethers 21 extend which connect to the proximal sleeve end 4 in different locations along its circumference, in order to avoid an unilateral anchoring pull that would tilt the proximal lumen opening 5.

The junction point 20 may be embodied by means of a second crimping tube 19 into which the tether 9 and the split tethers 21 are inserted and locked by crimping. Here too, the free ends of wire or cable material are preferably encapsulated inside the crimping tube 19.

The junction point 20 and split tethers 21 can be coated for protection as described in connection with the proximal tether attachment.

The connection of the split tethers 21 with the proximal sleeve end 4 can be embodied by means of the above described crimping method and crimping tubes or, alternatively, by means of an enlarged e.g. T-shaped end section of the split tethers 21 which may be received in a corresponding seat of a proximal mounting structure 22 of the sleeve 2.

The connection of the split tethers 21 with the proximal sleeve end 4 can be coated for protection as described in connection with the proximal tether attachment.

In accordance with an embodiment, an elastic spread ring 23 is supported by the proximal sleeve end 4 in a deformed wavy shape with undulations in a sleeve longitudinal direction but preferably with no or substantially no undulations in a sleeve radial or transverse direction, thereby elastically biasing the proximal sleeve end 4 in a radially spread configuration while preserving a continuously convex outer contour. This contributes to reliably seal the proximal sleeve end 4 against the surrounding tissue, e.g. a proximal duodenal wall section.

In order to exert the above said light outward pressure on the proximal end 4 of the sleeve 2 but avoid structural complexity due to excessive bending of the spread ring, the non-deformed circumferential length of the spread ring 23 is selected from 1.5 to 2.5, preferably about 2.0 times the diameter of the proximal sleeve end 4.

Within a proximal mounting structure 22 of the sleeve 2, two or more spread rings 23 may be arranged to increase the sealing area and to uniformly distribute the sealing pressure. The spread rings 23 and possible additional reinforcing inserts in the wall of the sleeve 2 can be e.g. grafted from NiTinol wire.

In order to further improve sealing, a proximal edge 24 (FIG. 2) of the proximal sleeve end 4 funnels radially outward and tapers proximally to form a thin sealing lip.

Further spread rings 23 may be connected to the sleeve 2 along its length to expand the sleeve and prevent it from twisting on itself These spread rings 23 could be connected either inside the sleeve, outside the sleeve or build within the wall of the sleeve.

In order to facilitate the connection of the spread ring 23 to the proximal sleeve end 4, a proximal reinforced semi-rigid tubular mounting structure 22 may be formed at the proximal sleeve end 4, which mounting structure 22 connects to the tether 9 or split tethers 21 and holds the spread ring 23. A less resistant and more flexible section of the sleeve (e.g. made of silicone with a durometer value of about 20 and a wall thickness of 0.125 inches or less) can be attached to or extend from a distal end of the mounting structure 22.

Figure 3:
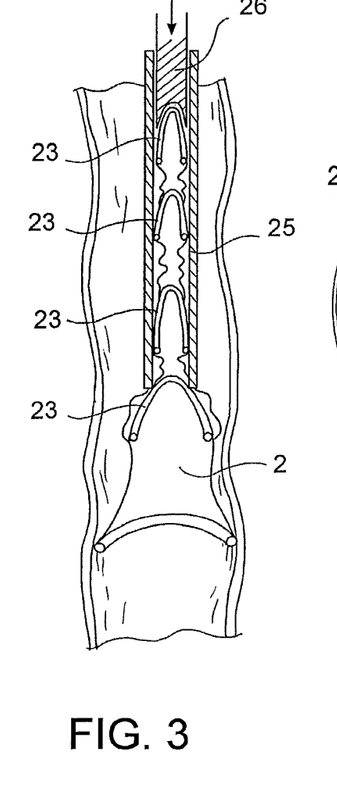
FIG. 3 illustrates a method step for endoluminal placement of the sleeve of an endoluminal sleeve device within the GI tract.

As shown in FIG. 3, during endoluminal placement of the duodenal sleeve device 1, the spread ring 23 or rings can be folded together with the sleeve 2 and packed inside a flexible insertion tube 25. A pusher 26 placed in the insertion tube 25 proximally (doctor's side) from the packed sleeve can then advance distally to push the sleeve out of the tube. The insertion tube 25 can be passed through an instrument channel of an endoscope or it can be attached laterally on the outside of the scope. The insertion tube 25 might also be introduced laparoscopically through a gastrostomy.

In accordance with some embodiments, the same insertion tube 25 may receive also the anchoring component 8 in its slender transport configuration either individually or together with the sleeve 2, so that also the anchoring component 8 or the entire sleeve device 1 can be transported into the GI tract by means of the insertion tube 25 and distally pushed out of the latter for deployment.

In accordance with a further embodiment, after placing and fastening of the proximal sleeve end 4 within the stomach or duodenum, the insertion tube 25 may be withdrawn and pulled endoluminally in a distal direction (e.g. by using an anal endoluminal access) to place the remaining sleeve section and spread rings 23 into the intestine. This method ensures that tension on the sleeve 2 is maintained during placement, preventing the sleeve from bunching up with a possible risk of blockage.

In accordance with embodiments, the spread ring 23 or rings can be either an add-on component to secure the sleeve 2 within the GI tract or it can be integrally connected to the sleeve 2.

The spread ring 23 can be additionally used to hold the sleeve lumen 3 and the gastric or duodenal wall open for ease of additional stapling and maintains the spacing of the fasteners. The spread ring 23 can carry markers showing planned locations for fasteners or for attachment of the split tethers 21.

In accordance with a further embodiment, additional spread rings 23 can be associated to the sleeve distally and proximally of the position of the sphincter of ODDI so that a sleeve wall between the two additional spread rings may create a bile collection space from which bile may be drained outside or inside the sleeve 2.

In accordance with a further embodiment, one or more (possibly adjustable) flanges 27, which might have an adjustable internal diameter, are connected inside the sleeve 2 for the purpose of varying the lumen size to influence gastric emptying or to create a torturous path for the chyme to slow the flow rate of the chyme through the section of the GI tract lined by the sleeve 2. Such internal flange 27 can further be configured to act as an anti reflux device of the sleeve. Conveniently, the flange 27 or flanges may be connected to the wall of the sleeve 2 near or by means of the spread rings 23.

FIGS. 6 and 7 show an elastic spring 28 interposed between the anchoring component 8 and the proximal sleeve end 4. The elastic spring 28 provides some additional flexibility during placement of the sleeve 2 end during expansion of the anchoring component 8 from the transport configuration to the deployed configuration. Moreover, the spring 28 can stretch and retract to adapt to gastric and duodenal peristaltic movements, while keeping the proximal sleeve end 4 in sealing engagement against the duodenal wall.

The spring 28 can be embodied by an elastic section of the tether 9 or of the split tethers 21 or may be interposed in series between the tether 9 and the proximal sleeve end 4 or between the tether 9 and the anchoring component 8. Also the spring 28 may be provided with an external protective layer as described for the tether assembly.

In accordance with an embodiment (FIG. 7) the spring 28 comprises an elastic coil connected to the proximal sleeve end 4, particularly to the proximal mounting structure 22 of the sleeve 2, wherein the elastic coil may be advantageously tapered in a proximal direction (towards the anchoring component 8). In this embodiment, a distal end of the flexible tether 9 may be connected to a proximal end of the tapered elastic coil, e.g. by crimping. The spring 28 or elastic tapered coil can also be formed in a single monolithic piece with the mounting structure 22 of the sleeve 2.

A coiled elastic spring 28 directly connected to the proximal sleeve end 4 may also improve the access to the proximal lumen opening 5 in comparison to a multiple split tether approach, compare FIGS. 1 and 7.

In an alternative embodiment, the elastic spring 28 is formed by a portion of the anchoring component 8 itself, e.g. by an elastic end section of the above described gastric coil 11 to which the proximal tether end 17 is connected.

The benefits of a large anchoring component 8 for anchoring the sleeve 2 and for obstruction prevention at the pylorus are thus combined with some desired elastic adjustment of the distance between the anchoring component 8 and the proximal sleeve end 4, thereby improving adaption to anatomy.

The sleeve device 1 comprises a distance adjusting mechanism 29 adapted to adjust the (non-stretchable) length of the tether 9 between the anchoring component 8 and the proximal sleeve end 4.

In some embodiments (FIGS. 8, 12), a plurality of tethers 9 are provided to connect the proximal mounting structure 22 of the sleeve 2 (placed within the proximal duodenum) to the anchoring component 8 which is preferably shaped as a ring (and placed proximal to the pylorus within the stomach), and the tethers 9 may be extended through the tissue of the pylorus 16 itself or through the pyloric passage without piercing the bodily tissue.

Figure 12:
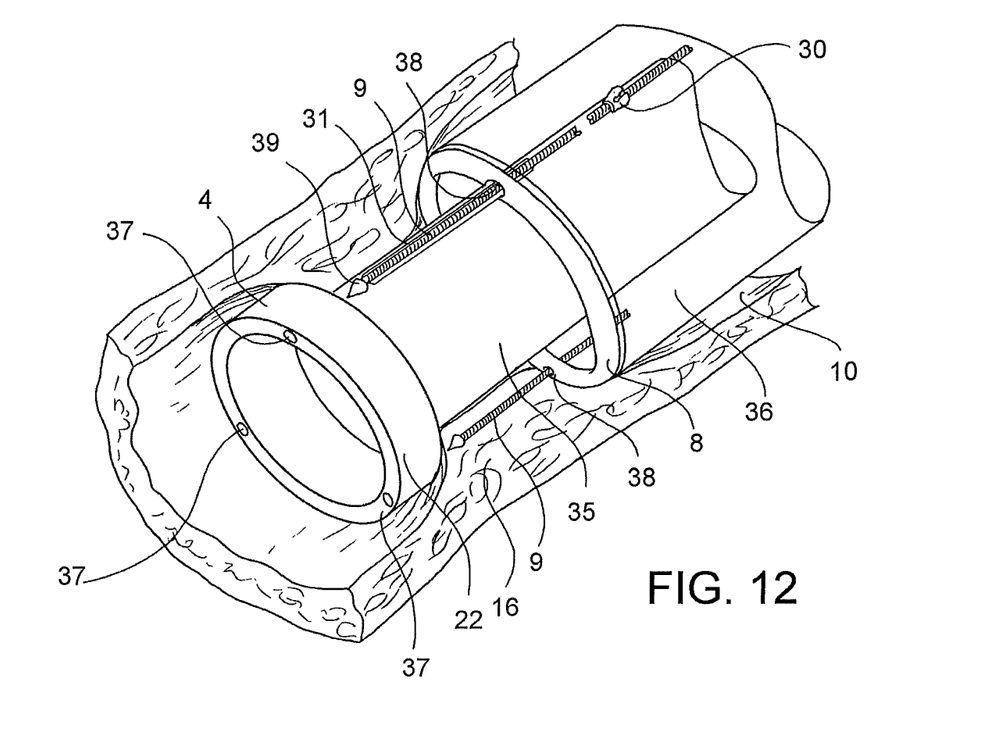
FIG. 12 illustrates devices and methods for anchoring a duodenal sleeve device in accordance with an embodiment.

The proximal ends 17 of the tethers 9 are inserted through holes in the anchoring component 22 and locked therein against distal withdrawal by collets or clamping slider 30 which can slide along the tether 9 and which can be locked in a selected position by a clamping mechanism 32, e.g. by a pusher which is elastically biased transversally into an internal channel of the clamping slider 30 through which the tether 9 is passed, said pusher having activating tabs which can be handled and activated by a grasper.

This allows to adjust the effective (non-stretchable) length of the tethers 9 and, thus, the distance between the anchoring component 8 and the proximal sleeve end 4.

In accordance with an embodiment (FIG. 12) the length of the tethers 9 is adjusted to place and hold the proximal sleeve end 4 and the anchoring component 8 snugly fitted against both sides of the pylorus 16.

The length adjustment of the at least one tether 9 can also be used to tighten up the anchoring component 8 and the proximal sleeve end 4 against the pylorus 16 to clamp the latter therebetween.

When the tethers 9 do not extend through the pylorus tissue but through the pylorus passage, a plurality of tethers can be extended diagonally therethrough in order not to rub against and irritate the delicate tissue at the pylorus.

During anchoring of the sleeve device 1 in the GI tract, the tethers 9 can be distally driven through the pylorus tissue or, generally towards and in coupling engagement with the proximal sleeve end 4, by means of a pushing tube 31 which receives the tether 9 inside and provides stiffness against flexure.

FIG. 12 illustrates a method and an endoscopic applier 33 comprising a flexible shaft and an applier head 34 arranged at a distal end of the flexible shaft. The applier head 34 comprises a proximal coupler mount 36 adapted to carry the (ring shaped) anchoring component 8, a distal coupler mount 35 operable to translate with respect to the proximal coupler mount 36 and adapted to carry the proximal mounting structure 22 of sleeve 2, as well as one or more pushing tubes 31 positioned and operable to translate through tether holes 38 formed in the anchoring component 8 with respect to both the proximal and distal coupling mounts 36, 35 and adapted to receive the tethers 9 provided with a distal (snap-) coupling tip 39 which may be pointed for piercing through bodily tissue. The applier 33 allows to adjust the distance between the anchoring component 8 and the proximal sleeve mounting structure 22 by translating the distal coupling mount 35 with respect to the proximal coupling mount 36 and to apply and fasten the tethers 9 by pushing them with the pushing tube 31 through the tether holes 38 in the anchoring component 8 and distally (through the pyloric tissue and) in engagement with coupling seats 37 formed in the sleeve mounting structure 22. After coupling and proximal withdrawal of the pushing tubes 31, the collets or clamping slider 30 can be advanced, adjusted and locked to fasten the tethers 9 to the anchoring component 8.

FIGS. 13 to 16 show an endoluminal sleeve device 1 for internally lining a section of the GI tract, which comprises a sleeve 2 configured for deployment inside a duodenum, the sleeve 2 having a wall of a flexible material defining a sleeve lumen 3, a proximal end 4 defining a proximal lumen opening 5, and a distal end 6 defining a distal lumen opening 7, as well as an anchoring component 8 having a slender transport configuration and a bulky deployed configuration, e.g. an expandable Nitinol ring, attached to the proximal sleeve end 4, e.g. by tethers as has been described herein before, or directly such that the anchoring component forms part of the proximal sleeve end 4. Anchoring of the sleeve device 1 can be accomplished by using an endoscopic applier to deliver a plurality of individual (plastic or metallic) hooking members 40 in a target anchoring location within the GI tract, e.g. near the pylorus 16, and to connect the individual anchoring members 40 along a circumferential row to the wall of the stomach 10 or of the intestine such that the hooking members 40 protrude radially into the lumen of the GI tract at the target anchoring location.

Figures 13, 14, 15, 16:
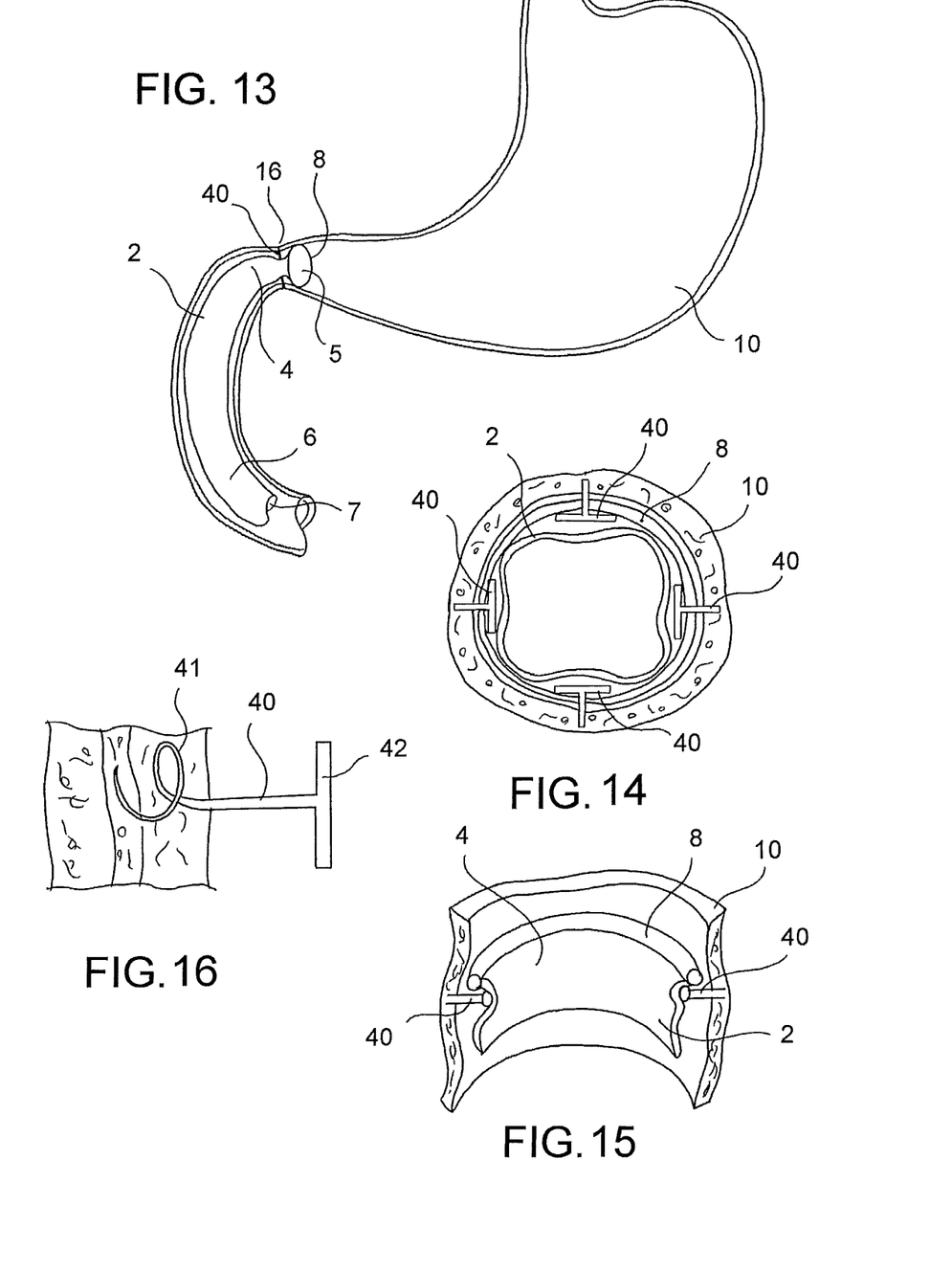
FIG. 13 illustrates a duodenal sleeve device implanted in a GI tract.
FIG. 14 is a cross-sectional view in the plane XIV-XIV in FIG. 13 in accordance with an embodiment.
FIG. 15 illustrates a detail of the anchored sleeve device in FIG. 13 in longitudinal cross-section in accordance with an embodiment.
FIG. 16 illustrates a detail of an anchoring member in accordance with an embodiment.

After placing the hooking members 40, the sleeve device 1 can be endoluminally inserted in the GI tract (using e.g. the methods described in relation with the embodiments of FIGS. 1 to 12) and the anchoring component 8 is positioned in the target anchoring location proximal to the circumferential row of hooking members 40. In response to a peristaltic distal pull, the anchoring component 8 will abut against the hooking members 40 and cannot pass distally through the target anchoring location. As illustrated in FIG. 16, the hooking member 40 may comprise a e.g. coiled or corkscrew shaped a tissue anchor 41 and a hook shaped catching portion 42 adapted to hook into the anchoring component 8 from a distal and radially internal side.

The sleeve 2 itself is sufficiently flexible to follow the curvature of the duodenum. Further, in some embodiments the walls of the sleeve are sufficiently flexible and/or collapsible to allow duodenal peristalsis to drive chyme through the lumen of the sleeve. Sufficient collapsibility of the walls of the sleeve prevents continuous intimate contact of the outer surface of the sleeve with the duodenal mucosa, avoiding damage to the duodenal mucosa and allowing digestive secretions not collected into the sleeve lumen to pass through the duodenal lumen outside the sleeve lumen.

In some embodiments, at least a portion of the wall of a sleeve may be porous or semipermeable to allow entry of digestive secretions into the sleeve lumen and/or to allow the flow of fluids and digested matter out of the sleeve lumen.

In some embodiments, at least a portion of the wall of a sleeve may be impermeable, analogous to the Endobarrier (R) by GI Dynamics Inc, Watertown, Mass., USA and as described in U.S. Pat. No. 7,267,694 which is included by reference as if fully set forth herein.

The diameter of the sleeve lumen may be substantially constant along the entire length of the liner tube. Although any suitable luminal diameter may be used, in some embodiments, the luminal diameter may be not more than about 30 mm, not more than about 25 mm and even not more than about 20 mm.

In some embodiments, the proximal end of the sleeve may be flared and may define a funnel-like structure.

The length of the sleeve may be any suitable length and may be selected in accordance with clinical decisions made by the treating physician. A typical sleeve is between about 25 cm and about 160 cm long. Generally, the sleeve is selected so that when the duodenal sleeve device is deployed, the distal lumen opening of the sleeve is located distal to the duodenal-jejunal flexure and empties out into the jejunum. In some embodiments, the sleeve may be even longer.

Suitable materials from which the sleeve are fashioned include silicone, polyurethane, polyethylene (e.g., low density polyethylene films) and fluoropolymers (e.g., expanded polytetrafluoroethylene). In some embodiments, the sleeve is fashioned from fluoropolymer or polyethylene film impregnated with polyurethane or silicone to reduce permeability, as taught in U.S. Pat. No. 7,267,694.

The sleeve may include one or more markers (e.g., barium) designed for viewing the position of the sleeve within the intestines through fluoroscopy, such as a longitudinal rib or other markers that are spaced along the length of sleeve. In addition, sleeve may further include components that inhibit twisting or kinking of the sleeve itself. In one embodiment, these components include one or more stiffening elements, such as rings, coupled to either the inside or the outside of the sleeve at spaced locations along its length. These rings can, for example, be made of a slightly thicker silicone material that would resist twisting or kinking of the sleeve around the ring. In other embodiments, the stiffening elements may be in spiral shape or extending lengthwise along at least a portion of the sleeve.

In an implantation method, the sleeve may be initially folded or rolled up and packed into the interior of an applier. The distal end of sleeve may be initially closed, e.g. with a small polymeric or silicone seal and forms a programmed tearing line, e.g. a perforation, along which the distal end can tear open by the internal pressure of the chyme flow.

Figure 17:
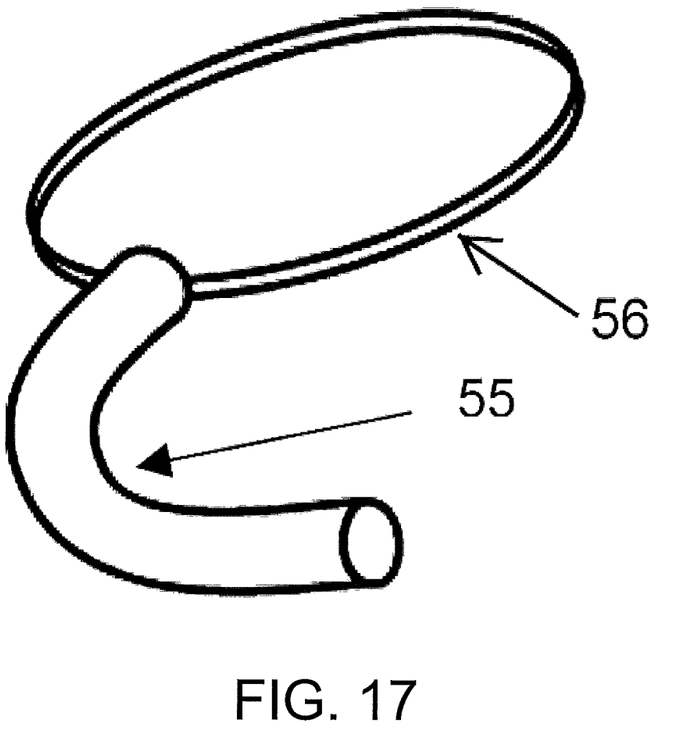
FIG. 17 illustrates an embodiment of a sleeve attached to an anchoring ring.

FIG. 17 shows an additional embodiment. The device in this figure has a hollow sleeve 55 attached to the ring 56. The sleeve 55 is designed to migrate down the duodenum and provide a barrier to nutrient absorption. The sleeve 55 may be used to locate or fix the device within the stomach, the shape of the ring 56 may be used to locate the device within the stomach, or the device may be fixed in place with suture, adhesive, anchors, etc.

Figure 18:
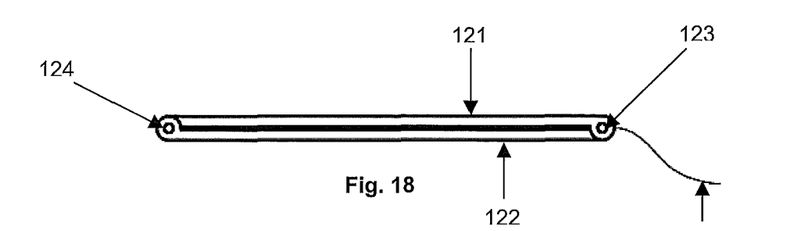
FIGS. 18-20 illustrate an embodiment of an expandable anchoring ring.

FIG. 18 shows an alternative embodiment of a ring 56 in which two flexible members 121 and 122 whose ends are attached at pivot points 123 and 124. A tensioning wire 125 is adjustably attached to pivot point 123 and rigidly attached to pivot point 124.

Figure 19:
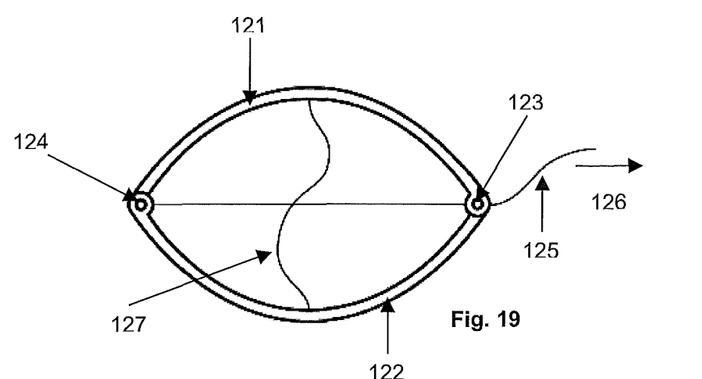

FIG. 19 shows steps in the deployment of the embodiment of FIG. 17. As the tensioning wire 125 is pulled in direction 126, the device expands from its flat insertion configuration to its final deployed expanded position. An additional tension wire 127 can be provided to better hold the device in its final configuration when acted upon by the natural movements of the stomach lumen.

Figure 20:
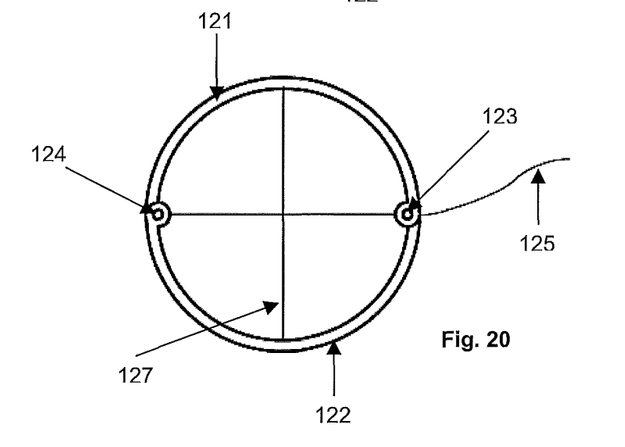

FIG. 20 shows the final, deployed configuration of the embodiment of FIG. 18. The length of members 121 and 122 and wires 125 and 127 can be selected or adjusted to define circular or elliptical deployed configurations.

Figure 21:
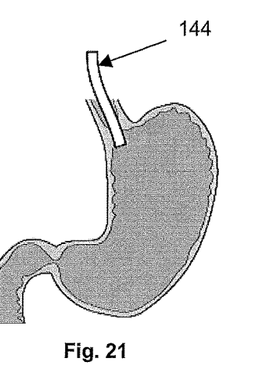
FIGS. 21-26 illustrate an embodiment of an expandable anchoring ring and steps for gastric implantation.

FIG. 21 shows a means of deploying and assembling the ring 56. In this embodiment, an insertion device 144 is intubated into the stomach. A lumen therein contains the ring 56 (FIG. 22) or alternatively, the ring 56 is passed through the insertion device 44.

Figure 22:
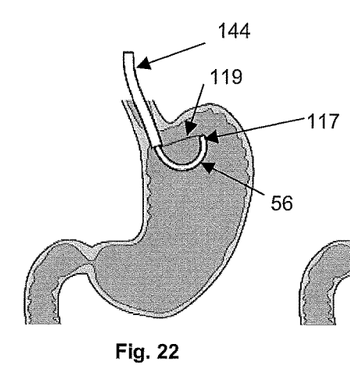

FIG. 22 shows a means of deploying and assembling the ring 56. This illustration shows the ring 56 being pushed from the lumen and into the stomach cavity while maintaining tension on cable 119, which is attached to the ring 56 at point 117.

Figure 23:
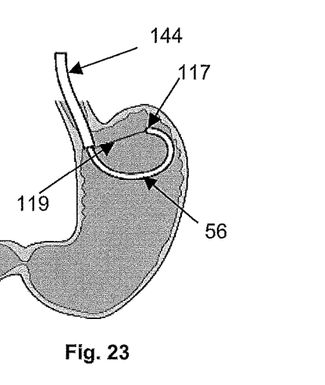

FIG. 23 shows a means of deploying and assembling the ring 56. This illustration shows the ring 56 being pushed further from the lumen and into the stomach cavity while maintaining tension on cable 119, which is attached to the device at point 117.

Figure 24:
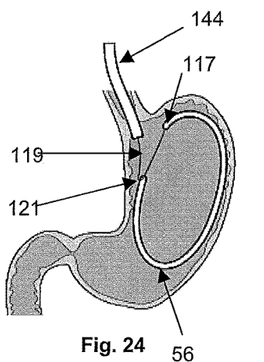

FIG. 24 shows a means of deploying and assembling the ring 56. This illustration shows the ring 56 being pushed completely from the lumen and into the stomach cavity while maintaining tension on cable 119, which is attached to the device at point 117. When the ring 56 has exited the insertion device 144, the wire is pulled through hole 121.

Figure 25:
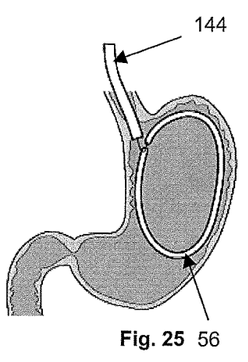

FIG. 25 shows a means of deploying and assembling the ring 56. This illustration shows tension being applied to cable 119 bringing both ends of the ring 56 together closing the device to its final configuration inside the gastric lumen.

Figure 26:
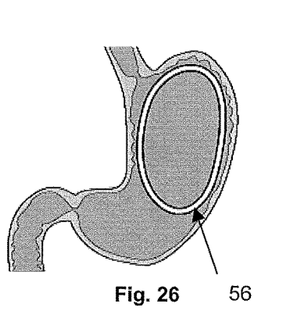

FIG. 26 shows a means of deploying and assembling the ring 56. This illustration shows the ring 56 in its final configuration. The final configuration of the device can be defined or driven by structures internal to the device such as the band described or by the tension in the stomach generated by the presence of the device.

Figure 27:
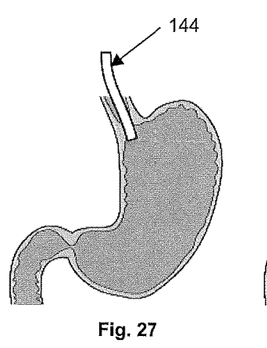
FIGS. 27-32 illustrate an embodiment of an expandable anchoring ring and steps for gastric implantation.

FIG. 27 shows an alternative means of deploying the ring 56. In this embodiment, an insertion device 144 is intubated into the stomach. A lumen therein contains the ring 56 (FIG. 28) or alternatively, the device is passed through the insertion device 144.

Figure 28:
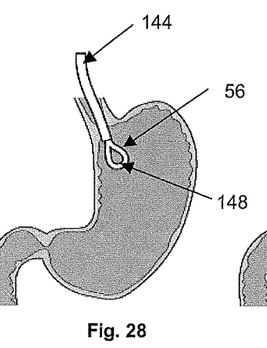

FIG. 28 shows the next step for deploying the ring 56. This illustration shows the ring 56 as it starts to exit the insertion device 144. The ring 56 is folded over onto itself at point 148.

Figure 29:
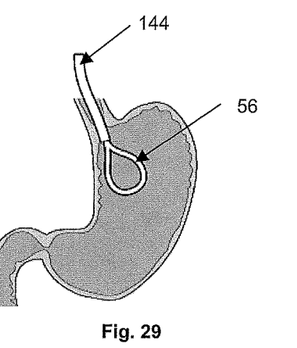

FIG. 29 shows the next step for deploying a closed loop embodiment of the ring. This illustration shows the ring 56 a bit further out of the insertion device 144. In this embodiment, point 148 is able to spring open once relieved from the insertion device 144.

Figure 30:
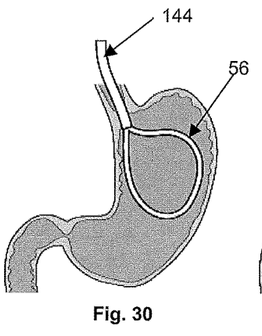

FIG. 30 shows the next step for deploying the ring 56. This illustration shows the ring 56 a bit further out of the insertion device 144. In this embodiment it can now be seen that the device is forming into its final expanded configuration.

Figure 31:
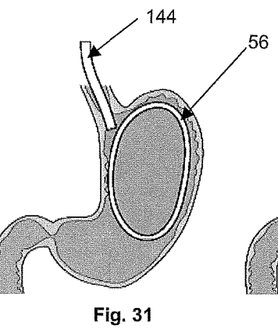

FIG. 31 shows the next step for deploying the ring 56. This illustration shows the ring 56 completely out of the insertion device 144 and in its final form, expanded and in contact with the stomach wall.

Figure 32:
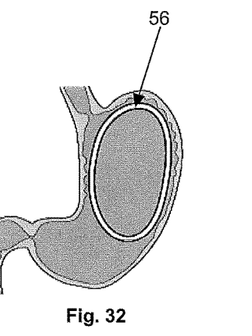

FIG. 32 shows the final step for deploying the ring 56. This illustration shows the ring 56 in its final form positioned within the stomach. The insertion device 44 has been removed finishing this portion of the procedure.

Figure 33:
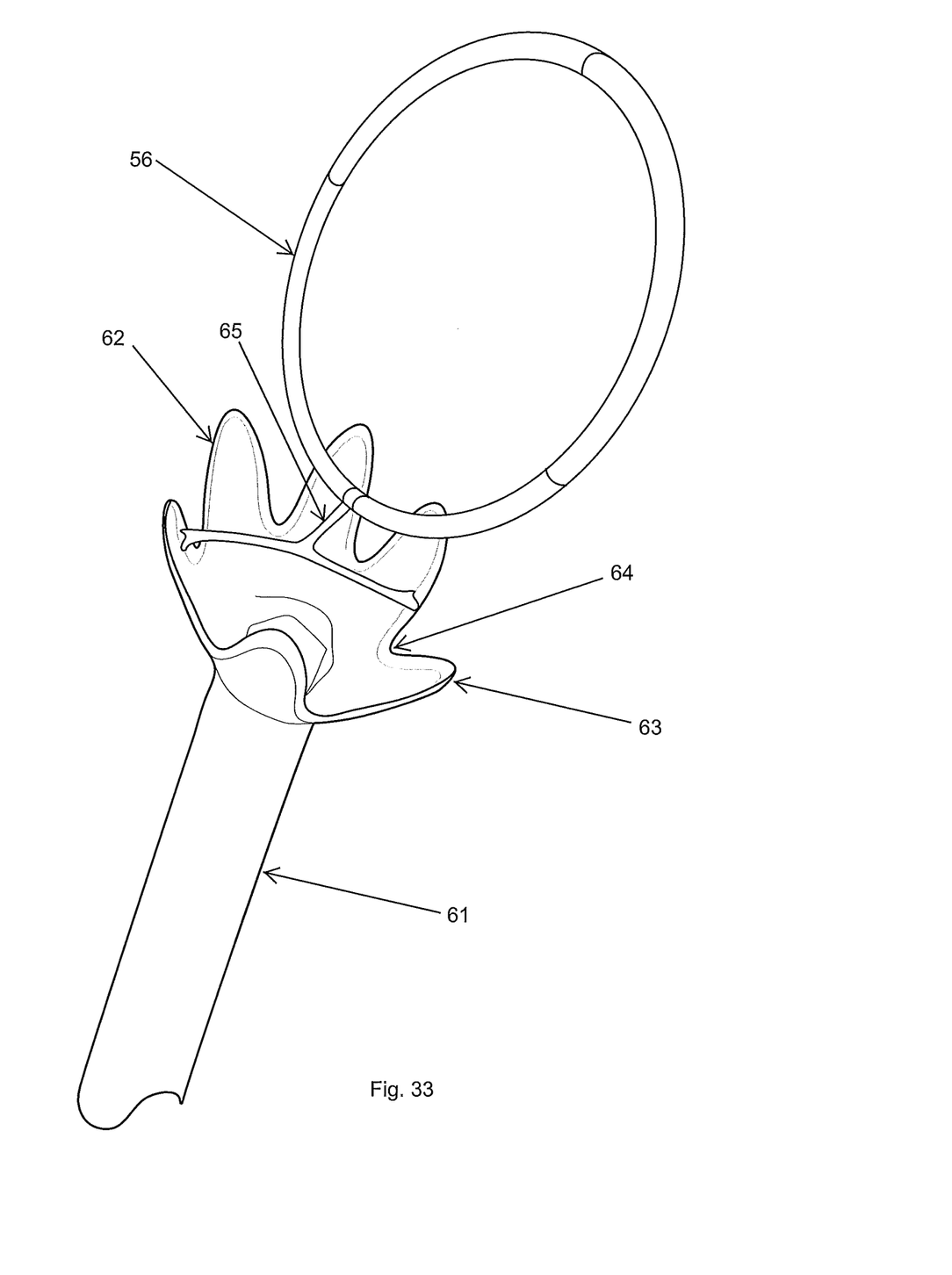
FIG. 33 illustrates an embodiment of a sleeve attached to an anchoring ring.

FIG. 33 shows an embodiment of a hollow sleeve 61 attached to the ring 56. Like the embodiments shown in FIGS. 1, 4, 6, 8 and 17, the sleeve 61 extends radially outward from the anchoring ring 56 and substantially in the same plane as the ring 56. The ring 56 can have a slender transport configuration and a bulky deployed configuration. In its deployed configuration (as shown in FIG. 33), the ring 56 diameter is larger than the pyloric opening so the ring 56 is prevented from passing into the duodenum, thus anchoring the ring 56 in the stomach. In one embodiment, the ring 56 can have a composite construction comprising a resilient spring metal center, such as nitenol, encapsulated in an elastomeric sheath. The sleeve 61 is designed to migrate down the duodenum and provide a barrier to nutrient absorption. The proximal end of the sleeve 61 comprises an elastic spread ring 62 supported by the proximal sleeve end in a deformed wavy shape with undulations having a plurality of peaks 63 and valleys 64. The spread ring 62 radially biases the proximal end of the sleeve 61 into a funneled configuration. The spread ring 62 can be a spring metal embedded in the sleeve 61. The ring 56 is connected to the sleeve 61 with a tether 65. As shown in this embodiment, the tether 65 has a generally inverted T-shape and extends radially outward from the ring 56. The tether 65 bridges the proximal opening of the sleeve 61 and is attached on opposite ends to the spread ring 62.

In this way bypass conduits can be created in the GI tract of a patient to achieve a malabsorptive effect in cases where such an effect may enhance weight loss, as well as the initially described effects on hormonal signaling in general.

Particularly, the described devices and procedures obviate undesired migration of the sleeve away from its original anchoring position and addresses the need of reliable sealing of the lined lumen. Moreover, some embodiments of the described devices and methods are beneficial with regard to permitting normal biological events, including vomiting, to occur.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. An endoluminal sleeve device for internally lining a section of the GI tract, comprising:
   a sleeve configured for deployment inside a duodenum, the sleeve having walls of a flexible material defining a sleeve lumen, a proximal end defining a proximal lumen opening, and a distal end defining a distal lumen opening; and a ring attached to the proximal end of the sleeve, sized to remain within the stomach and having a circumferential outer surface;

wherein the circumferential outer surface of the ring is oriented perpendicular to the orientation of the proximal lumen opening of the sleeve.

2. The endoluminal sleeve device of claim 1, wherein the proximal end of the sleeve is connected to the ring with a tether.

3. The endoluminal sleeve device of claim 2, further comprising at least one elastic spread ring supported by the proximal sleeve end in a deformed wavy shape with undulations in a sleeve longitudinal direction, wherein the spread ring elastically biases the proximal sleeve end in a radially spread configuration while preserving a continuously convex outer contour.

4. The endoluminal sleeve device of claim 1, wherein a proximal edge of the proximal sleeve end forms a funneled shaped sealing lip.

5. The endoluminal sleeve device of claim 1, further comprising an elastic spring interposed between the ring and the proximal sleeve end.

6. The endoluminal sleeve device according to claim 5, wherein said spring is formed by an elastic section.

7. The endoluminal sleeve device according to claim 5, in which the spring comprises an elastic coil connected to the proximal sleeve end and tapered in a proximal direction towards the ring.

8. The endoluminal sleeve device of claim 2, wherein a length of the tether between the ring and the proximal sleeve end is adjustable.

9. An endoluminal sleeve device for internally lining a section of the GI tract, comprising:

a sleeve configured for deployment inside a duodenum, the sleeve comprising a proximal end and a distal end: and a ring attached to the proximal end of the sleeve, the sleeve extending radially outward from the ring.

10. The device of claim 9, wherein the ring is substantially planar, and the sleeve extends radially outward from the ring and substantially in the same plane as the ring.

11. The device of claim 10, wherein the ring comprises a slender transport configuration and a bulky deployed configuration.

12. The device of claim 11, further comprising at least one elastic spread ring biasing the proximal end of the sleeve in a radially spread configuration.

13. The device of claim 12, wherein the elastic spread ring comprises a spring with longitudinal undulations supported by the proximal end of the sleeve.

14. Endoluminal sleeve device anchoring system, comprising an endoluminal sleeve device according to claim 1 and an applier with a flexible shaft and an applier head arranged at a distal end of the flexible shaft, the applier head comprising:

a proximal coupler mount adapted to carry the ring, a distal coupler mount operable to translate with respect to the proximal coupler mount and adapted to carry a ring-shaped proximal mounting structure of sleeve, at least one pushing tube adapted to receive a tether and operable to translate with respect to both the proximal and distal coupling mounts through tether holes formed in the ring and towards a coupling seat formed in the sleeve mounting structure, the tether being provided with a distal coupling tip adapted to connect with the coupling seats in the sleeve mounting structure.

* * * * *